US008186506B2

(12) United States Patent
Kanios et al.

(10) Patent No.: US 8,186,506 B2
(45) Date of Patent: *May 29, 2012

(54) PACKAGING SYSTEM FOR TRANSDERMAL DRUG DELIVERY SYSTEMS

(75) Inventors: David P. Kanios, Miami, FL (US); Juan A. Mantelle, Miami, FL (US); Paul Johnson, Miami, FL (US); Chensheng Li, Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 2031 days.

This patent is subject to a terminal disclaimer.

(21) Appl. No.: 11/130,325

(22) Filed: May 16, 2005

(65) Prior Publication Data

US 2005/0214354 A1    Sep. 29, 2005

Related U.S. Application Data

(63) Continuation of application No. 10/051,220, filed on Jan. 18, 2002, now Pat. No. 6,905,016, which is a continuation-in-part of application No. 09/804,926, filed on Mar. 13, 2001, now abandoned.

(60) Provisional application No. 60/285,976, filed on Apr. 23, 2001, provisional application No. 60/189,333, filed on Mar. 14, 2000.

(51) Int. Cl.
*B65D 81/26* (2006.01)

(52) U.S. Cl. .............. 206/204; 206/484; 206/484.1; 220/23.83

(58) Field of Classification Search ........... 206/204, 206/438, 439, 363; 424/448, 449; 428/34.3, 428/34.7, 35.2; 220/23.83
See application file for complete search history.

(56) References Cited

U.S. PATENT DOCUMENTS

| | | | | |
|---|---|---|---|---|
| 4,777,780 A * | 10/1988 | Holzwarth | ...... | 53/432 |
| 4,813,541 A * | 3/1989 | Velasco et al. | ...... | 206/459.1 |
| 4,814,168 A * | 3/1989 | Sablotsky et al. | ...... | 514/182 |
| 4,943,435 A * | 7/1990 | Baker et al. | ...... | 424/448 |
| 5,008,110 A * | 4/1991 | Benecke et al. | ...... | 424/448 |
| 5,322,161 A * | 6/1994 | Shichman et al. | ...... | 206/204 |
| 5,698,217 A * | 12/1997 | Wilking | ...... | 424/448 |
| 6,054,153 A * | 4/2000 | Carr et al. | ...... | 426/87 |
| 6,054,196 A * | 4/2000 | Koch et al. | ...... | 428/34.3 |

* cited by examiner

*Primary Examiner* — J. Gregory Pickett
*Assistant Examiner* — Raven Collins
(74) *Attorney, Agent, or Firm* — Foley & Lardner LLP (57) ABSTRACT

A device and method for stabilizing a drug, particularly a chiral drug or the active enantiomer(s) thereof, in a carrier composition of a transdermal delivery system prior to the systems use by providing a product packaging system to prevent or control degradation reactions that can result from certain packaging materials and moisture contamination, while at the same time providing a child-resistant wrapping for the transdermal system.

30 Claims, 2 Drawing Sheets

PACKAGING SYSTEM FOR TRANSDERMAL DRUG DELIVERY SYSTEMS

This application is a Continuation Application of U.S. patent application Ser. No. 10/051,220 filed Jan. 18, 2002, which claims the benefit of U.S. Provisional Application No. 60/285,976, filed Apr. 23, 2001. U.S. Ser. No. 10/051,220 is a CIP of U.S. patent application Ser. No. 09/804,926, filed Mar. 13, 2001 now abandoned which claims the benefit of U.S. Provisional Application 60/189,333 filed Mar. 14, 2000.

BACKGROUND OF THE INVENTION

1. Field of the Invention

The present invention relates to stabilizing a drug in a packaged product. More specifically, the present invention relates to a packaging system for the prevention of degradation in pharmaceutical products, particularly controlled release drug delivery devices such as transdermal systems.

2. Description of Related Art

The use of transdermal drug delivery systems or "patches" as a means to topically administer a drug is well known. Such systems dissolve or disperse the drug into a carrier composition, such as a polymeric and/or pressure-sensitive adhesive composition, from which the drug is delivered. These transdermal drug delivery systems typically are affixed adhesively to the skin or mucosa of a user, and the drug diffuses at a controlled rate from a polymer reservoir or layer into the skin or mucosa and absorbed into the blood. Such transdermal systems are described, for example, in U.S. Pat. Nos. 4,814,168, 4,994,267, 5,474,783, 5,656,286, 5,958,446 and 6,024,976, all of which are expressly incorporated by reference in their entireties.

The typical packaging system for a transdermal system involves enclosing it within a packaging material that is sealed to form a container, such as a sealed pouch, in which the system may remain for long periods of time before its removal and use. Several factors must be considered to ensure the storage stability of a packaged transdermal system.

Conventional transdermal systems that incorporate solid or crystalline forms of drugs require that such drugs be dissolved in the polymeric and/or pressure-sensitive adhesive composition in order to deliver a therapeutically effective amount. The ability of a transdermal system to deliver a therapeutically effective amount for the intended duration of use therefore requires that the active agent remain in non-crystalline or dissolved form in the carrier composition prior to use.

The ability of a transdermal system to deliver a therapeutically effective amount for the intended duration of its use further requires that the drug remain stable in its active form (i.e., not degrade, convert, decompose or the like). The therapeutic activity of many drugs is associated with their absolute molecular configuration. Many drugs exist as different structural forms that have the ability to rotate the plane of plane-polarized light (are "chiral"). In describing such drugs, the prefixes D and L or R and S are used to denote the absolute configuration of the molecule about its chiral center(s) The prefixes d and 1 or (+) and (−) are employed to designate the sign of rotation of plane-polarized light by the compound, with (−) or 1 meaning that the compound is levorotatory. A compound prefixed with (+) or d is dextrorotatory. There is no correlation between nomenclature for the absolute stereochemistry and for the rotation of an enantiomer. Thus, D-lactic acid is the same as (−) lactic acid, and L-lactic acid is (+). For a given chemical structure, these chiral compounds exist as a pair of enantiomers (called stereoisomers) which are identical except that they are non-superimposable mirror images of one another. A specific stereoisomer may also be referred to as an enantiomer, and a mixture of such isomers is often called an enantiomeric or racemic mixture.

Preventing drug degradation can be critical since 50 of the top 100 drugs worldwide exhibit chirality. See, for example, S. C. Stinson, Chemical & Engineering News, American Chemical Society, Washington, D.C., Vol. 76 (Sep. 21, 1998) pg. 83; and "Chiral Drugs," S. C. Stinson, Chemical & Engineering News, American Chemical Society, Washington, D.C., (Oct. 9, 1995). A case in point is provided by the L-form of the beta-adrenergic blocking agent, propranolol, which is known to be 100 times more potent than the D-enantiomer. Moreover, certain isomers may actually be deleterious rather than simply inactive or inert. For example, it is suggested that the D-enantiomer of thalidomide is a safe and effective sedative when prescribed for the control of morning sickness during pregnancy, while the corresponding L-enantiomer is believed to be a potent teratogen.

Accordingly, any packaging material used to enclose a transdermal system must not absorb, react with, or otherwise adversely affect the drug or other excipients or components used in the transdermal system. For example, U.S. Pat. No. 5,008,110 discloses that certain polyolefin materials used for transdermal devices tend to absorb lipophilic solvents and/or enhancers, which can significantly decrease the drug's solubility in the carrier composition, as well as cause physical failure of the packaging material. U.S. Pat. No. 4,943,435 discloses that nicotine will adversely affect many common transdermal system component materials such as adhesives, membranes, backings and release liners. It has been additionally discovered that methylphenidate, a chiral drug that exists as four enantiomers of which only one is currently known to be significantly pharmacodynamically active, is unstable in the presence of certain types of packaging materials used for transdermal systems.

It is further known that common environmental factors such as the presence of water (in liquid or vapor form), air and light can adversely affect the stability of some drugs. See, for example, U.S. Pat. No. 5,077,104. Such environmental factors can further affect the solubility of the drug in the carrier composition, which in turn can also significantly impact the shelf-life of the transdermal system. For example, the presence of moisture tends to promote crystal growth or formation in many drugs during storage of a transdermal system. Since only solubilized drug is available for delivery out of a transdermal system, any packaging material used to enclose a transdermal system must provide for the control against such environmental factors.

In the manufacture of a packaged transdermal system, the interior of the sealed package may, and often does, contain trapped moisture. The origin of such moisture can include incidental amounts in the transdermal system components or environmental exposure present when the transdermal system was first packaged. To prevent or control the amount of moisture within such a sealed package, various methods have been employed. These methods include drying of raw materials, further drying of the transdermal system or storing in a desiccating atmosphere prior to packaging, vacuum packaging or packaging in a dry room.

However, the ability to prevent or eliminate moisture within the sealed package, especially over long periods of storage, is further dependent on the moisture permeability of the packaging materials. As a result, packaging materials produced of multiple layers, many incorporating metal foils, are typically required to provide an environmental barrier. Such packaging requirements often result in higher costs for materials and production, and require controlled production to achieve a uniform and desired level of moisture impermeability. Such packages may be difficult to open without the aid of mechanical means such as scissors, and, even the best, may still be moisture permeable to some extent.

Although careful control of the manufacturing conditions and packaging materials can reduce the presence of moisture within a sealed pouch containing a transdermal system, the further use of a desiccant is still often required.

The use of a desiccant in packaging products is generally known in the packaging industry. For example, U.S. Pat. No. 5,322,161 discloses a package for packaging moisture sensitive materials. In the '161 patent, the desiccant is present in a desiccant pouch. The desiccant can be molecular sieves and silica gels. The package of the '161 patent also includes heat-sealing layers for sealing the package.

Desiccant materials have also been used in conjunction with pharmaceutical products. For example, U.S. Pat. No. 5,698,217 discloses a method for inhibiting precipitation of a drug in a transdermal system that forms a solid hydrate in the presence of water vapor. The '217 patent achieves this by placing a desiccant material sealed within the same product package containing transdermal system. The desiccant material is further enclosed within its own package. Accordingly, a desiccant-containing package is required for each individual transdermal system. Further, both such desiccant packaging and desiccant materials must be carefully selected to ensure suitability and compatibility (i.e., control problem of contamination) with the drug and other components of the transdermal system to which they are in close proximity or contact.

U.S. Pat. No. 6,050,400 discloses a packaging system for moisture sensitive pharmaceutical substances comprising an inner container permeable to moisture enclosed within an outer container less permeable to moisture and containing a desiccant. The '400 patent does not teach the use of a pouch for transdermal systems that is permeable to moisture vapor while at the same time meeting the requirements for child-resistant packaging.

None of the related art teaches a cost efficient packaging system for transdermal drug delivery systems that incorporates within a container use of a desiccant and a moisture permeable pouch to hold the transdermal system which is inert to the drug and other transdermal components, in order to prevent degradation reactions of the drug that can be caused by contamination from certain packaging materials and moisture, while also providing a child-resistant wrapping for the transdermal system. In addition, none of the related art teaches the importance of controlling packaging materials and moisture to prevent degradation reactions of chiral drugs or pharmaceutically active enantiomer(s) thereof in transdermal systems.

The present invention is directed to stabilizing a drug, particularly a chiral drug or the pharmaceutically active enantiomer(s) thereof, in a carrier composition of a transdermal system prior to the systems use by providing a product packaging system to prevent or control degradation reactions that can result from contamination by certain packaging materials and moisture, while at the same time providing a child-resistant wrapping for the transdermal system.

SUMMARY OF THE INVENTION

It is therefore an object of this invention to provide a cost efficient packaging system for a transdermal drug delivery system that improves protection from contamination, such as the crystallization or degradation, of the drug, and from other environmental factors, during storage of the system prior to its use.

It is therefore another object of this invention to provide a packaging system for a transdermal system that will not significantly absorb, react with, or otherwise adversely affect the drug or other excipients or components used in the transdermal system during storage of the system prior to its use.

It is also an object of this invention to provide a packaging system that provides the physical characteristics to meet the requirements for child-resistant packaging.

It is a further object of this invention to provide a packaging system for a transdermal system that improves the stability of chiral drugs and pharmaceutically active enantiomers thereof contained in a transdermal system during its storage prior to its use.

It is still another object of this invention to provide a method for making a packaging system from materials that permit visual inspection of their contents.

The foregoing and other objects are achieved with this invention by providing a pouch for a transdermal system that is inert to the components of the transdermal system, water vapor permeable to permit removal of moisture from within the pouch, and child-resistant. The pouched transdermal system is further sealed within a substantially water vapor impermeable product package that contains a desiccant material. The drug incorporated in the transdermal system remains substantially solubilized and stable in the carrier composition of the transdermal system free of contamination from the desiccant or moisture while the system is stored in the product package prior to its use.

DETAILED DESCRIPTION OF THE INVENTION

The term "topical" or "topically" is used herein in its conventional meaning as referring to direct contact with an anatomical site or surface area on a mammal including skin, teeth, nails and mucosa.

The term "mucosa" as used herein means any moist anatomical membrane or surface on a mammal such as oral, buccal, vaginal, rectal, nasal or ophthalmic surfaces.

The term "transdermal" as used herein means passage into and/or through skin or mucosa for localized or systemic delivery of an active agent.

As used herein, "therapeutically effective" means an amount of drug that is sufficient to achieve the desired local or systemic effect or result, such as to prevent, cure, diagnose, mitigate or treat a disease or condition, when applied topically over the duration of intended use. The amounts necessary are known in the literature or may be determined by methods known in the art, but typically range from about 0.1 mg to about 20,000 mg, and preferably from about 0.1 mg to about 1,000 mg, and most preferably from about 0.1 to about 500 mg per human adult or mammal of about 75 kg body weight per 24 hours.

The term "system" as used herein is intended to broadly mean a transdermal drug delivery device topically applied to a mammal for the purposes of providing some beneficial or therapeutic effect, and includes all patch-type devices commonly referenced in the art as reservoir, matrix, adhesive matrix, in-line, membrane and multi-layer devices, iontophorectic devices, and medicated bandages and pads. Further details and examples of transdermal systems generally are described in U.S. Pat. Nos. 4,994,267, 5,006,108, 5,446,070, 5,474,787, 5,656,286, 5,719,197, and Ser. Nos. 60/115,987 and 09/163,351, all of which are assigned to Noven Pharmaceuticals, Inc. and incorporated herein by reference.

The term "carrier composition" as used herein refers to any non-aqueous material known in the art as suitable for transdermal drug delivery administration, and includes any polymeric material into which a drug may be solubilized, alone or in combination or admixture with the other additives and excipients including solvents, permeation enhancers, diluents, stabilizers, fillers, clays, buffering agents, biocides, humectants, anti-irritants, antioxidants, preservatives, plasticizing agents, cross-linking agents, flavoring agents, colorants, pigments and the like. Regardless of the type of transdermal system used to practice the invention, the carrier composition is preferably substantially free of water (i.e., the composition contains less than about 10% water by weight, preferably less than about 5% by weight, and most preferably less than about 3% water by weight based upon the total weight of the composition prior to its topical application).

The term "solubilized" is intended to mean that in the carrier composition there is an intimate dispersion or dissolution of the active agent at the crystalline, molecular or ionic level. As such, the active agent is considered herein to be in "non-crystallized" form when in the compositions of the present invention.

As used herein, the term "degradation" refers to any change to a drug in a transdermal system that may occur during storage resulting in (a) an undesirable by-product, for example by hydrolysis or oxidation of the drug, or undesirable form, such as crystals, or (b) loss of the drug, for example through absorption into other materials within the transdermal system or pouch, or evaporation.

As used herein, a "product package" is broadly defined to refer to a sealed package substantially impermeable to water vapor that defines a space to contain and surround a pouch-sealed transdermal system and a desiccant material within the product package. The term "substantially impermeable to water vapor" means that the product package has a moisture vapor transmission rate not greater than about 0.0002 g/day/in. sq. at 40° C./75% Relative Humidity (RH). Therefore, for a typical shelf life of two years, the product package should permit not greater than about 1 g of moisture to pass through at 25° C./60% RH.

As used herein, the term "pouch" is broadly defined to refer any packaging material containing or covering a transdermal system and is sealed on at least one side. A pouch can comprise two sheets or laminates of the packaging material of this invention that has been joined along all its edges. It may also comprise a single sheet or laminate that has been folded and sealed all along its edges, or along all non-folded edges. It may further comprise a bag or pocket that is sealed along one or more edges. The perimeter of the pouch can be in any design, shape or form, irregular or uniform. Uniform shapes such as squares, rectangles, circles and ovals are preferred in order to facilitate the sealing and manufacturing processes. Sealing can be accomplished by heat, ultrasound, laser, or adhesive and the like. The preferred packaging material is self-sealing (i.e., able to form a stable bond between two facing surfaces of the same material without the use of an adhesive).

In order to effectively achieve the mechanical strength characteristics to be called "child-resistant" (i.e., substantially impairs a child's ability to open a container with its hands as determined in accordance with the procedures set forth in the Requirements for the Special Packaging of Household Substances with changes cited in the *Federal Register*, Vol. 60, No. 140, pp. 37710-3744, 1995), a bi-layered structure for the pouch is preferred. While a single film or sheet could be employed, it would require a corresponding thickness that may affect the other desired properties such as permeation to moisture vapor and self-sealing ability as well as increased packaging costs.

Figure 1:
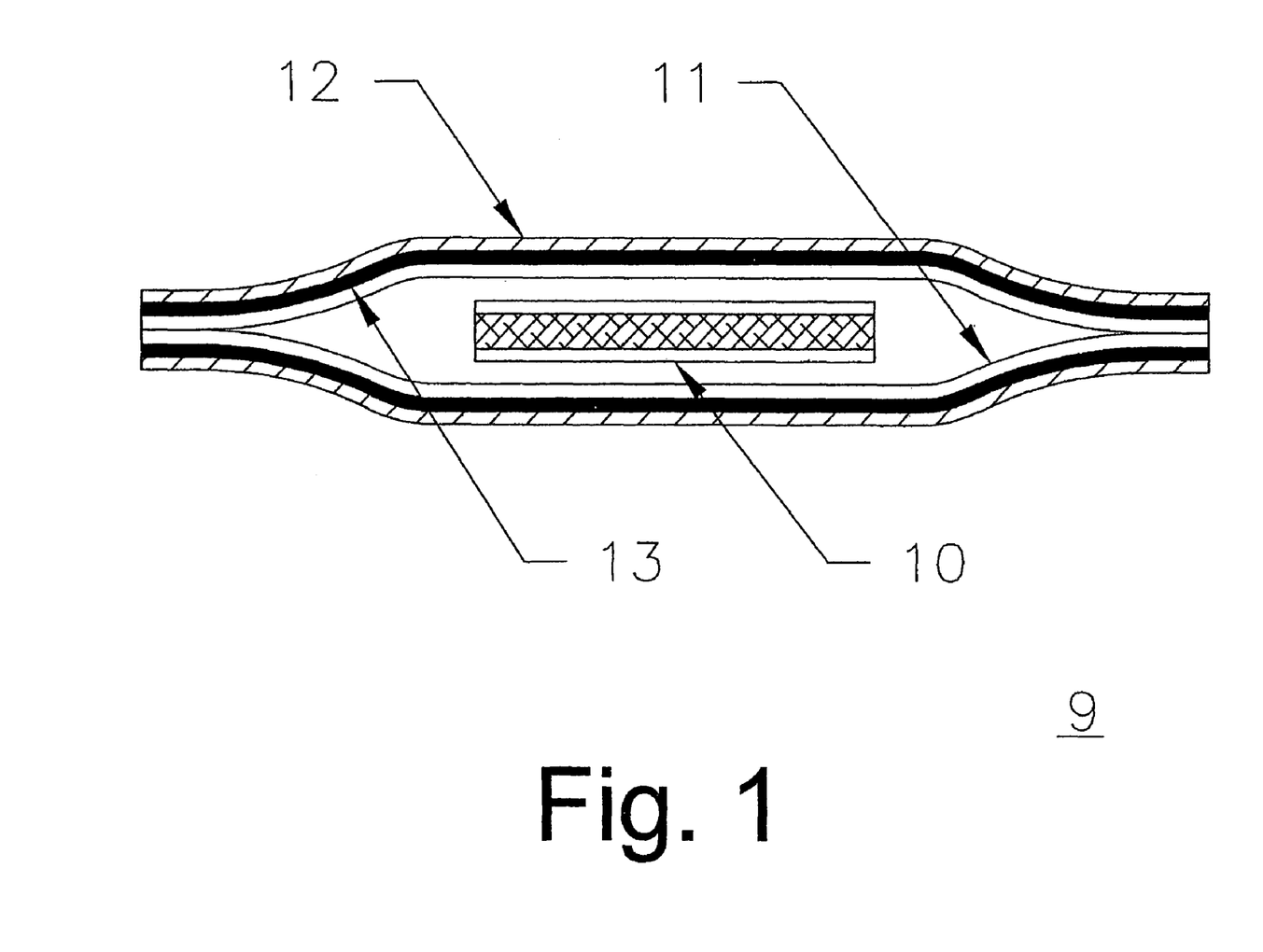
FIG. 1 is a cross-sectional illustration of the pouch in the embodiment of a bi-layered structure.

The preferred packaging material for use as primary layer 11 of the pouch is a thermoplastic polymer that does not absorb, react with, or otherwise adversely affect the drug or other excipients or components used in the transdermal system. A particularly preferred thermoplastic material is nitrile rubber modified acrylonitrile-methyl acrylate copolymers. Such materials are disclosed, for example, in U.S. Pat. No. 3,426,102, and are commercially sold under the trademark Barex® by BP Chemicals, Inc., Cleveland, Ohio. Various material compositions of Barex® resins are available, for example, Barex® 210, 2218 (which has a higher rubber modified content than 210), and 214. An especially preferred material is Barex® 210.

In practice of the preferred embodiments of the invention, the thickness of primary layer 11 is from about 0.5 mil to about 2.5 mil, more preferably from about 0.75 mil to about 1.5 mil, and even more preferably from about 1.0 mil to about 1.5 mil. While thinner and thicker widths may be employed, inner layer 11 should not be so thin so as to compromise its permeation and stabilizing properties, nor too thick so as to adversely affect its self-sealing and packaging properties.

Secondary layer 12 can be a sheet or laminate comprising metal foils, polyethylenes, polyesters, vinyl acetate resins, ethylene/vinyl acetate copolymers, polyurethanes, polyvinyl chloride, woven and non-woven fabric, cloth and papers. In practice of the preferred embodiments of the invention, the thickness of secondary layer 12 is from about 0.2 mil to about 3.0 mil, more preferably from about 0.2 mil to about 1.5 mil, and even more preferably from about 0.5 mil to about 1.0 mil. While thinner and thicker widths may be employed, secondary layer 12 should not be so thin so as to compromise its permeation and tear resistance properties to the pouch, nor too thick so as to adversely affect sealing to primary layer 11 or packaging properties of the pouch.

Particularly preferred materials for use as secondary layer 12 have a higher melting temperature than the primary layer in order to provide a heat sealable structure, and are also translucent (i.e., impart visual clarity) such that the ability to view and inspect the contents of the pouch is not lost. The preferred secondary layer 12 material is a polyester. Particularly preferred polyesters are those commercially sold under the trademark Mylar® and Melinex® by E.I. du Pont de Nemours and Company, Wilmington, Del., and include Mylar® S, Melinex® S and Melinex® 800 polyester films.

Secondary layer 12 can be affixed to primary layer 11 by any technique known in the art. Attachment by means of heat fusion or an adhesive, particularly a pressure-sensitive adhesive, is preferred. Use of an adhesive is preferred in order to achieve greater tear resistance properties which are desirable in creating child resistant/proof packaging.

An adhesive is a pressure-sensitive adhesive within the meaning of the term as used herein if it has the properties of a pressure-sensitive adhesive per se or if it functions as a pressure-sensitive adhesive by admixture with tackifiers, plasticizers, cross-linking agents or other additives.

Pressure-sensitive adhesives include all of the non-toxic natural and synthetic polymers known or suitable for use in transdermal systems including solvent-based, hot melt and grafted adhesives, and may be used alone or in combinations, mixtures or blends. Examples of suitable adhesives include polyacrylates, polysiloxanes, silicones, rubbers, gums, polyisobutylenes, polyvinylethers, polyurethanes, styrene block copolymers, styrene/butadiene polymers, polyether block amide copolymers, ethylene/vinyl acetate copolymers, and vinyl acetate based adhesives. Suitable polysiloxanes include those commercially available and sold under the trademark BIO-PSA® by Dow Corning Corporation, Midland, Mich.

The pressure-sensitive adhesives particularly useful in practicing this invention include polyacrylates of one or more monomers of acrylic acids or other copolymerizable monomers. Polyacrylate adhesives also include polymers of alkyl acrylates and/or methacrylates and/or copolymerizable secondary monomers, or monomers with functional groups. The term "polyacrylate" is intended to be used interchangeably with the terms acrylic, acrylate and polyacrylic as used herein and as known in the art. Suitable pressure-sensitive acrylic adhesives are commercially available and include those sold under the trademark DURO-TAK® by National Starch and Chemical Company, Bridgewater, N.J., and GELVA® Multipolymer Solution by Solutia, Inc., St. Louis, Mo.

In practice of the preferred embodiments of the pouch, the adhesive is applied to secondary layer 12 and dried to a thickness that should preferably not exceed about 1 mil, and is preferably in a range from about 0.3 mil to about 0.75 mil, prior to pressure sealing the adhesive coated secondary layer 12 to primary layer 11.

Whatever material or structure is used to form a pouch that does not significantly absorb, react with, or otherwise adversely affect the drug or other excipients or components used in the transdermal system, while at the same time meeting the requirements for child-resistant packaging, it must also be permeable to moisture vapor to allow its removal by an external desiccant. Preferably, the pouch is preferentially permeable to moisture vapor over non-water components or drug of the transdermal system. The term "preferentially permeable to moisture vapor" means that the pouch has a moisture vapor transmission rate not greater than about 2.5 g/hr/m sq. at 40° C./95% RH as determined pursuant to the American Society of Testing and Materials (ASTM) for moisture vapor transmission, ASTM E-96-95.

In order to provide protection from light for drugs, which may further be subject to degradation by light, it may be desirable to use a modified form of secondary layer 12 material. For example, the material may be tinted to provide a partial barrier affecting only certain wavelengths of light, or be substantially opaque as in a metalized polyester film.

Reference to FIG. 1 shows a cross-sectional view of a preferred embodiment of pouch 9 containing transdermal system 10 according to the present invention. The primary layer 11 comprising a nitrile rubber modified acrylonitrile methyl-acrylate copolymer is affixed to secondary layer 12 comprising a polyester by means of adhesive 13. The laminate in the form of pouch 9 may be sealed at the edges for example by heat.

The present invention is generally directed to an improved packaging system for transdermal systems containing methylphenidate. Methylphenidate exists as four enantiomers which are the (2R:2'R)-(+)-threo-enantiomer, the (2S:2'S)-(−)-threo-enantiomer, the (2R:2'S)-(+)-erythro-enantiomer, and the (2S:2'R)-(−)-erythro-enantiomer, but only the d-threo-methylphenidate is currently known to be significantly active. An "active" enantiomer refers to the isomer of a chiral drug that exhibits greater pharmacodynamic activity than its counterpart enantiomers. The major degradants include ritalinic acid and the erythro-enantiomers (both d:1 and 1:d). The term "degradant" as used herein refers to any impurity, metabolite, non-metabolite, enantiomer and the like that exhibits no or significantly lower pharmacodynamic activity for a particular therapeutic purpose or deserved beneficial effect than the drug molecule or another enantiomer thereof.

In the presence of moisture, methylphenidate was observed to form ritalinic acid by hydrolysis. Exposure to moisture was further found to result in the formation of the erythro-enantiomers. While not wishing to be bound by a particular scientific theory, it is believed that such degradation reaction involves the formation of enolates as reaction intermediates, which then undergo auto-oxidation or racemization. In non-aqueous carrier compositions that provide low or nonpolar environments, water facilitates the formation of enolates by lowering the overall degradation reaction's activation energy. Accordingly, other drugs that contain ketone, aldehyde, ester or benzyl functional groups, such as norenthindrone, norethindrone acetate, and estradiol, and also form enolates would benefit by prevention of moisture contamination in transdermal systems.

Although the particularly preferred embodiments of the present invention are generally directed to transdermal systems containing methylphenidate, particularly in free base form, packaging materials useful in the present invention are useful for systems containing any drug that is incompatible (unstable) with commonly used packaging materials as those described in the examples herein (such as polyethylene or polypropylene). Such drugs include chiral drugs, for example, ceftriaxone, thalidomide, propranolol, ibuprofen, ketoprofen, naproxen, peroxetine, finasteride, sertraline, paclitaxel, terfenadine, verapamil, enalapril, lisinopril, ifosamide, methyldopa, indacrinone, bupivacaine, loxiglumide, amlodipine, pyridinium, levoslmedan, ondansetron, salmeterol, ketorolac, doxazosin, cisapride, albuterol, oxybutynin, selective serotonin reuptake inhibitors such as fluoxetine, loratadine, fexofenadine, cetirizine, formoterol, triptans such as sumatriptan, doxazosin, zolpidem, sibutramine, atorvastatin, nadolol, abacavir, citalopram, nifedipine, glitazones such as troglitazone, progliotazone, and rosiglitazone, clorazepate, lorazepam, oxazepam, temazepam, omeprazole, levofloxacin, captopril, and diltiazem.

It is to be understood that while the description of the exemplary embodiments herein are primarily directed to transdermal systems containing methylphenidate, particularly in free base form, the present invention also encompasses any drug that that forms crystals or degradants in the presence of moisture.

The term "drug" as used herein is intended to have the broadest meaning possible, and be used interchangeably with active agent, pharmaceutical, medicament and any substance intended to provide a beneficial effect including a therapeutic, prophylactic, pharmacological, or physiological substance, cosmetic and personal care preparations, and mixtures thereof. More specifically, any substance that is capable of producing a pharmacological response, localized or systemic, irrespective of whether therapeutic, diagnostic, cosmetic or prophylactic in nature, is within the contemplation of the invention. It should be noted that the drugs could be used singularly or in combinations and mixtures. While there is no limitation on the type of active agent that can be used in this invention, drugs that are solid at room temperature are preferred.

The active agents contained in the carrier composition can be in different forms depending on the solubility and release characteristics desired, for example as neutral molecules, components of molecular complexes, and pharmaceutically acceptable salts, free acids or bases, or quaternary salts of the same. Simple derivatives of the drugs such as pharmaceutically acceptable ethers, esters, amides and the like which have desirable retention and release characteristics but which are easily metabolized at body pH, and enzymes, pro-active forms, pro-drugs and the like, can also be employed.

The product package of the invention should isolate and protect its contents from the ambient environmental factors, such as water vapor, air and light, that can adversely affect them. Suitable materials for use as the product package are well known in the art and include polyethylenes, polyesters, polypropylenes, polyurethanes, polyolefin, polyvinyl alcohol, polyvinyl chloride, polyvinylidene, polyamide, vinyl acetate resins, BAREX®, ethylene/vinyl acetate copolymers, ethylene/ethylacrylate copolymers, metal-vapor deposited films or sheets thereof, rubber sheets or films, expanded synthetic resin sheets or films, non-woven fabrics, foils and papers. Such materials may be used singularly, in combination, as laminates (cold sealed, heat sealed or flood or pattern coated with natural or synthetic adhesives) or as coextrusions, so long as they impart the desired permeation and barrier properties from ambient environment.

The product package may be configured in any manner, and may be flexible or rigid. It may comprise two sheets joined along all its edges. It may also comprise a single sheet or laminate that has been folded and sealed all along its edges, or along all non-folded edges. It may further comprise a bag or pocket that is sealed along one or more edges. Alternatively, the product package may be molded or formed into the shape of an open container, such as a tub or box, and sealed around the periphery with a cover or lid made from a second sheet of packaging material. The cover or lid may be made of the same or a different packaging material, and be re-sealable. When using a sheet of packaging material for the cover, a laminate with foil, paper or nylon is preferred in order to create a suitable surface for printing product information and provide sufficient moisture impermeability. Sealing may be accomplished by any suitable method such as by means of pressure for conventional lid closures, or by laser, heat, ultrasound, adhesive, and the like.

Figure 2:
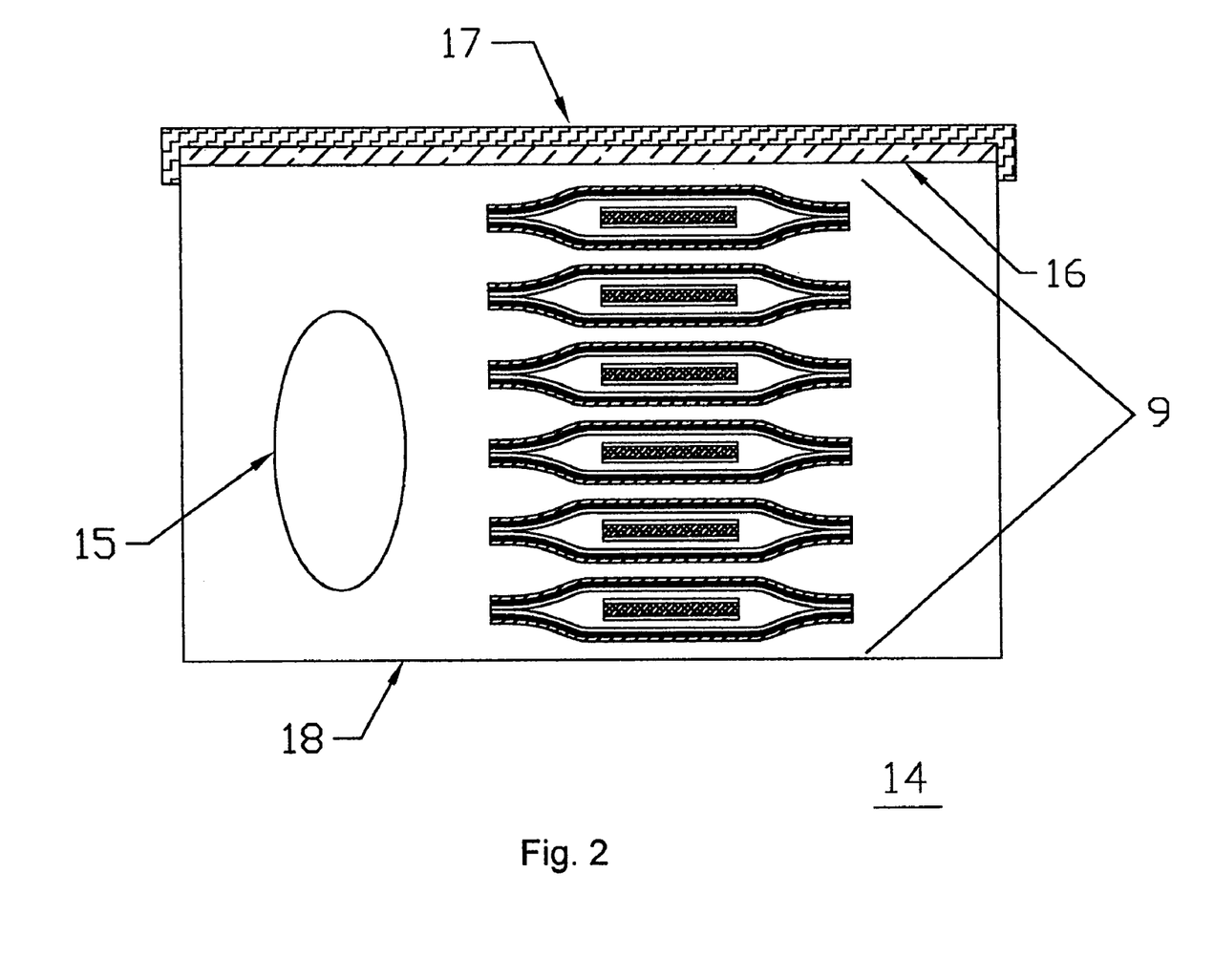
FIG. 2 is a cross-sectional view of a product package comprising transdermal system-containing pouches, which pouch is in the embodiment of a bi-layered structure, and a desiccant.

In a preferred embodiment, the product package is substantially rigid and comprises a base sheet 18 of 46 mil polypropylene formed into the shape of an open tub. Polypropylene is a relatively inexpensive material, can be used singularly as a sheet, is easy to mold or form into the desired shape, and is recyclable. A coextensive laminate cover sheet 16 of 5 mil polyethylene/foil/nylon is then heat-sealed to the tub opening. A reusable lid made of a suitable packaging material such as polyester or polypropylene may further be used in order to continue to maintain the pouched transdermal systems in a desiccating environment after removal of the cover sheet 16 until the supply of systems is exhausted.

The size of the container should be sufficient to accommodate at least a one-month supply of pouched transdermal systems (i.e., about 30) and up to a three-month supply. A product package having a surface area of about 35 sq. in. is preferred to accommodate such contents together with the desiccant material.

The type of desiccant material that may be used will depend on the nature of the components of the transdermal device, and can be determined by one skilled in the art through routine experimentation. Suitable materials for use as desiccants include oxides of aluminum, calcium, titanium, zirconium, silicon, thorium, magnesium and barium, alumina, alumina hydrates, natural and synthetic molecular sieves, silica gel, precipitated silica, clays, perchlorates, zeolite, natural gums, magnesium or calcium sulfate, calcium, lithium or cobalt chloride, and calcium carbonate. While moisture selective desiccant materials, such as molecular sieves, may be used, use of a pouch that substantially prevents or controls permeation of the drug or any non-water high vapor pressure components or other excipients, such as glycols, or drug is preferred. An indicator dye can also be added to the desiccant material to provide for monitoring the amount of moisture absorbed during storage of the product package. Suitability or Compatibility of the Desiccant Material with a Particular Transdermal System The amount of desiccant that may used will depend on several factors including the moisture permeability of the types of materials used in making the pouch and product package, the moisture absorbing capacity of the particular desiccant material, and the intended shelf life of the transdermal system. The minimal amount to be used is that amount that will effectively absorb water vapor within the product package over the intended shelf life of the transdermal system, typically two years, and achieve an acceptable level of drug loss from crystallization or degradation to still deliver a therapeutically effective amount of the drug. The desiccant should be capable of absorbing at least about 1.5 grams to about 5 grams of moisture over the intended period of storage and use of the product package. The amount of desiccant material needed to prevent such moisture contamination can be determined by one skilled in the art through routine experimentation.

In a preferred embodiment of the packaging system comprising transdermal systems containing methylphenidate in heat-sealed pouches of Barex®/adhesive/polyester laminates enclosed within a polypropylene product package, the preferred desiccant material is silica gel in an amount of about 4-5 grams.

The suitable desiccant material may be incorporated into the product package in any manner including a compressed pellet, or enclosed within a holder such as a capsule, sachet or container. Any material that is water vapor permeable and does not react with or adversely affect (for example, by leaching or absorption) components of the transdermal system or other materials used in making the pouch and product package is suitable for forming the desiccant holder. Such materials include polyethylene, polyethylene terephthalate, polypropylene, coated and non-coated paper, and perforated sheet and laminate materials. A preferred material for the desiccant holder is a non-woven polyolefin.

The packaging system may be prepared by loading the product package contents (i.e., pouch and desiccant) by means of any suitable or conventional manufacturing operation and sealing process. Reference to FIG. 2 shows a cross-sectional view of product package 14 according to a preferred embodiment of the present invention comprising multiple pouches 9 of FIG. 1, desiccant 15, base sheet 18, cover sheet 16 and reusable lid 17.

EXAMPLES

The following procedure is illustrative of how to generally prepare a transdermal system, and particularly describes the transdermal systems used in testing pouches of various packaging materials described in the examples.

A transdermal system containing methylphenidate in free base form and comprised of a racemate of about 50% each of d-threo-methylphenidate and 1-threo-methylphenidate in a pressure-sensitive adhesive carrier composition was prepared by combining 6.0 parts methylphenidate base along with 4.5 parts of ethyl cellulose (Ethocel® 20, Dow Chemical Corp., Midland, Mich.) in 22.75 parts of ethyl acetate. Next, 8.6 parts of a polyacrylate adhesive (GMS 3067; Solutia Inc., St. Louis, Mo.) and 24.5 parts of a polysiloxane adhesive (BIO-PSA® 7-4302; Dow Corning Corp., Midland, Mich.) were added and thoroughly mixed. The carrier composition was then wet caste at 20 mils, with a wet gap bar, onto a fluorocarbon release liner (Scotch Pak® 1022, 3M, Minneapolis, Minn.) and run through an oven to evaporate volatile solvents. The dry composition was laminated to a (polyester) backing film (Scotch Pak® 1012, 3M, Minneapolis, Minn.). The carrier composition had the ingredient concentrations on a dry weight basis as shown below.

| Ingredient | Dry Weight % |
|---|---|
| Polysiloxane Adhesive (BIO-PSA ® 7-4302) | 50 |
| Polyacrylate Adhesive (GMS 3067) | 15 |
| Ethyl Cellulose (Ethocel ® 20) | 15 |
| Methylphenidate Base | 20 |
|  | 100 |

Transdermal system samples of 10 $cm^2$ were then die cut and placed into 2.5 $in^2$ heat-sealed pouches comprised of the various material combinations described in each of the following examples.

Example 1

A 1.25 mil film of Barex® 210 heat laminated to 0.35 mil aluminum foil. The aluminum foil was then bonded to 35# Kraft paper using an adhesive (laminate material manufactured by Richmond Technology, Redlands, Calif.).

Example 2

A 1.25 mil film of Barex® 210 laminated with a polyester film using a urethane adhesive commercially available as 94035 and sold by Lawson Mardon (Shelbyville, Ky.).

Example 3

A 1.25 mil film of Barex® 210 laminated with aluminum foil using an adhesive, which is then laminated to a polyester film using an adhesive, which is commercially available as 90580 and sold by Lawson Mardon.

Example 4

A 1.25 mil film of Barex® 210 (provided by Greenway Plastics Industries Corporation, Wayne, N.J.).

Example 5

Same as Example 1.

Example 6

A 2.0 mil film of Scotch Pak® 1012 (a polyester film laminated to a ethylene/vinyl acetate heat seal layer manufactured by 3M).

Example 7

A 2.0 mil film of Scotch Pak® 1009 (a polyester film laminated with aluminum foil and ethylene/vinyl heat seal layer manufactured by 3M).

Example 8

A 3 mil film of a proprietary laminate barrier film commercially available as 5488-9913 and sold by Kappler Protective Apparel & Fabrics, Inc. (Guntersville, Ala.).

Example 9

A 1.25 mil film of Barex® 210 laminated to a 2 mil polyester film using an acrylate adhesive (Duro-Tak® 87-2296 by National Starch and Chemical Corporation, Bridgewater, N.J.).

Example 10

Same as Example 9 except a 0.92 mil polyester film was used.

Example 11

Same as Example 9 except that a 0.2 mil polyester film was used.

Example 12

A 3 mil film of a proprietary laminate barrier film commercially available as 5488-99A and sold by Kappler Protective Apparel & Fabrics, Inc.

Example 13

A 2 mil polyester film.

Example 14

A 1.25 mil film of Barex® 210 heat-sealed into pouch within a heat-sealed pouch of 2 mil polyester.

Three samples of each example containing the transdermal system were then placed in an oven at 80° C. for 4 days to accelerate aging (i.e., simulate shelf-life storage of about 2 years). The transdermal systems were then removed from the pouches, and placed in an extraction solution of acidified methanol after removal of the release liner. The extraction solution containing the system was sonicated for 45 minutes at room temperature. Aliquot samples were then extracted and examined by high-pressure liquid chromatography to determine and measure the percent of degradants and active drug loss.

The same extraction procedure was employed to the pouch materials to determine and measure the amount of active drug (i.e., d-threo-methylphenidate) absorbed such materials in mg by dry weight. The results are set forth in Table I.

TABLE I

| Example | Total Degradation % | Drug Loss (%) | Drug Absorption (mg) |
|---|---|---|---|
| 1* | 0.1 | 0 | 0.108 |
| 2 | 9.7 | 10.1 | 0.440 |
| 3 | 25.3 | 23.7 | 0.254 |

TABLE I-continued

| Example | Total Degradation % | Drug Loss (%) | Drug Absorption (mg) |
|---|---|---|---|
| 4 | 8.6 | 6.2 | 0.265 |
| 5 | 15.0 | 14.1 | 0.209 |
| 6 | 8.3 | 16.9 | 2.979 |
| 7 | 8.6 | 19.2 | 3.182 |
| 8 | 8.5 | 12.1 | 1.692 |
| 9 | 8.7 | 7.9 | 0.176 |
| 10 | 8.7 | 6.6 | 0.107 |
| 11 | 8.6 | 6.9 | 0.117 |
| 12 | 8.7 | 21.4 | 2.217 |
| 13 | 8.6 | 4.8 | 0.204 |
| 14 | 8.7 | 6.2 | 0.147 |

*Example 1 was used as a control which was maintained at room temperature for 4 days.

Significant drug loss is also observed in the presence of vinyl acetate. The examples using the Barex® and polyester film laminates demonstrated good stability over time.

The effect of using a desiccant to control degradation caused by moisture contamination was tested in transdermal system samples (as prepared above) of 25 cm$^2$ placed into 2.5 in$^2$ heat-sealed pouches comprised of the materials described in Example 10.

Approximately 40 pouches were each placed in two desiccators impermeable to the transmission of water vapor. In one desiccator, the bottom was lined with granules of a desiccating salt, calcium sulfate. The desiccators were then placed in an oven at 40° C. and 75% relative humidity for one month to accelerate aging. After removing the pouches from the desiccators, three pouches were randomly selected from each and the transdermal systems contained therein were placed in an extraction solution of acidified methanol after removal of the release liner. The extraction solution containing the system was sonicated for 45 minutes at room temperature. Aliquot samples were then extracted and examined by high-pressure liquid chromatography to determine and measure the percent of the major degradants, ritalinic acid (RA) and erthryo isomer (EI).

The same extraction procedure was also employed to determine and measure the amount of the major degradants in a three samples from a control group of pouches which were maintained refrigerated at 8° C. and 2% relative humidity to minimize susceptibility to degradation at room temperature. The results are set forth in Table II.

TABLE II

| Example | % RA | % EI | Total % Degradants |
|---|---|---|---|
| Non-Desiccated 1 | 2.60 | 2.27 | 4.87 |
| Non-Desiccated 2 | 2.57 | 2.26 | 4.81 |
| Non-Desiccated 3 | 2.57 | 2.27 | 4.81 |
| Desiccated 1 | 0.33 | 0.69 | 1.02 |
| Desiccated 2 | 0.34 | 0.67 | 1.01 |
| Desiccated 3 | 0.34 | 0.69 | 1.03 |
| Control 1 | 0.34 | 0.32 | 0.66 |
| Control 2 | 0.32 | 0.32 | 0.64 |
| Control 3 | 0.33 | 0.30 | 0.63 |

What is claimed is:

1. A product package for preventing degradation of a drug in a transdermal delivery system comprising:
    (a) an outer package comprised of a substantially moisture impermeable material and configured to contain and surround (i) a desiccant and (ii) one or more inner pouches;
    (b) a desiccant contained within said outer package and outside of said one or more inner pouches;
    (c) one or more inner pouches comprised of a moisture-permeable material and configured to contain and surround a transdermal delivery system; and
    (d) a transdermal delivery system comprising a drug, wherein said transdermal delivery system comprises a backing and release liner and is contained within each of said one or more inner pouches.

2. The product package according to claim 1, wherein said one or more inner pouches is child-resistant.

3. The product package according to claim 1, wherein said one or more inner pouches is comprised of an inner layer and an outer layer.

4. The product package according to claim 3, wherein said transdermal delivery system comprises a drug and other components, and wherein said inner layer of said one or more inner pouches is comprised of a thermoplastic material that does not react with or absorb said drug or other components.

5. The product package according to claim 3, wherein said outer layer of said one or more inner pouches at least partially protects said transdermal delivery system from light.

6. The product package according to claim 3, wherein said inner layer of said one or more inner pouches comprises a nitrile rubber modified acryolnitrile-methyl acrylate copolymer and said outer later of said one or more inner pouches comprises a polyester.

7. The product package according to claim 3, wherein said inner and outer layers of said one or more inner pouches are affixed to each other by means selected from the group consisting of heat or adhesive.

8. The product package according claim 1, wherein said outer package comprises a material selected from the group consisting of polyethylenes, polyesters, polypropylenes, polyurethanes, polyolefin, polyvinyl alcohol, polyvinyl chloride, polyvinylidene, polyamide, vinyl acetate resins, nitrile rubber modified acryolnitrile-methyl acrylate copolymers, ethylene/vinyl acetate copolymers, ethylene/ethylacrylate copolymers, metal-vapor deposited films or sheets, rubber sheets or films, expanded synthetic resin sheets or films, non-woven fabrics, foils, and papers.

9. The product package according to claim 8, wherein said outer package comprises a thermoplastic material.

10. The product package according to claim 9, wherein said outer package comprises polypropylene.

11. The product package according to claim 1, wherein said desiccant is capable of absorbing at least 1.5 g of moisture over a one year storage period.

12. The product package according to claim 1, wherein said drug is a moisture-sensitive drug.

13. The product package according to claim 1, wherein said drug is a chiral drug.

14. The product package according to claim 1, wherein said drug is methylphenidate.

15. The product package according to claim 1, wherein said product package comprises two or more inner pouches, each containing and surrounding a transdermal delivery system.

16. A transdermal product package for improving the stability of chiral drugs and pharmaceutically active enantiomers thereof comprising:
    (a) an outer package comprised of a substantially moisture impermeable material and configured to contain and surround (i) a desiccant and (ii) one or more inner pouches;
    (b) a desiccant contained within said outer package and outside of said one or more inner pouches;

(c) one or more inner pouches comprised of a moisture-permeable material and configured to contain and surround a transdermal delivery system; and (d) one or more transdermal delivery systems comprising a chiral drug or pharmaceutically active enantiomer thereof, wherein said transdermal delivery system comprises a backing and release liner and is contained within each of said one or more inner pouches.

17. The product package according to claim 16, wherein said one or more inner pouches is child-resistant.

18. The product package according to claim 16, wherein said one or more inner pouches is comprised of an inner layer and an outer layer.

19. The product package according to claim 18, wherein said transdermal delivery system comprises a drug and other components, and wherein said inner layer of said one or more inner pouches is comprised of a thermoplastic material that does not react with or absorb said drug or other components.

20. The product package according to claim 18, wherein said outer layer of said one or more inner pouches at least partially protects said transdermal delivery system from light.

21. The product package according to claim 18, wherein said inner layer of said one or more inner pouches comprises a nitrile rubber modified acryolnitrile-methyl acrylate copolymer and said outer layer of said one or more inner pouches comprises a polyester.

22. The product package according to claim 18, wherein said inner and outer layers of said one or more inner pouches are affixed to each other by means selected from the group consisting of heat or adhesive.

23. The product package according to claim 16, wherein said outer package comprises a material selected from the group consisting of polyethylenes, polyesters, polypropylenes, polyurethanes, polyolefin, polyvinyl alcohol, polyvinyl chloride, polyvinylidene, polyamide, vinyl acetate resins, nitrile rubber modified acryolnitrile-methyl acrylate copolymers, ethylene/vinyl acetate copolymers, ethylene/ethylacrylate copolymers, metal-vapor deposited films or sheets, rubber sheets or films, expanded synthetic resin sheets or films, non-woven fabrics, foils, and papers.

24. The product package according to claim 23, wherein said outer package comprises a thermoplastic material.

25. The product package according to claim 24, wherein said outer package comprises polypropylene.

26. The product package according to claim 16, wherein said desiccant is capable of absorbing at least 1.5 g of moisture over a one year storage period.

27. The product package according to claim 16, wherein said chiral drug or pharmaceutically active enantiomers thereof is a moisture-sensitive drug.

28. The product package according to claim 16, wherein said chiral drug or pharmaceutically active enantiomers thereof is methylphenidate.

29. The product package according to claim 16, wherein said product package comprises two or more inner pouches, each containing and surrounding a transdermal delivery system.

30. The product package according to claim 16, wherein degradation of said chiral drug or enantiomer thereof in said transdermal delivery system is diminished as compared to a corresponding transdermal delivery system that is not packaged in said inner pouch and outer package.

* * * * *